(12) United States Patent
Simon et al.

(10) Patent No.: US 6,228,348 B1
(45) Date of Patent: *May 8, 2001

(54) COMPOSITION IN THE FORM OF AN OIL-IN-WATER EMULSION COMPRISING AN ACRYLIC TERPOLYMER AND ITS USES, IN PARTICULAR ITS COSMETIC USES

(75) Inventors: Pascal Simon, Vitry sur Seine; Dominique Bordeaux, Longpont sur Orge, both of (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/503,196

(22) Filed: Feb. 14, 2000

(30) Foreign Application Priority Data

Mar. 17, 2000 (FR) .................................................. 99 03320

(51) Int. Cl.[7] ................ A61K 7/42; A61K 7/00
(52) U.S. Cl. .......................... 424/59; 424/401; 424/70.1
(58) Field of Search ................ 424/59, 60, 400, 424/407; 514/880, 844–846

(56) References Cited

U.S. PATENT DOCUMENTS 6,060,041 * 5/2000 Candau et al. ................ 424/59

FOREIGN PATENT DOCUMENTS

| 0 173 109 | 3/1986 | (EP) . |
| 0 250 943 | 1/1988 | (EP) . |
| 0 262 465 | 4/1988 | (EP) . |
| 0 268 164 | 5/1988 | (EP) . |
| 0 388 582 | 9/1990 | (EP) . |
| 0 613 682 | 9/1994 | (EP) . |

* cited by examiner

*Primary Examiner*—Shelley A. Dodson
*Assistant Examiner*—Konata M. George
(74) *Attorney, Agent, or Firm*—Oblon, Spivak, McClelland, Maier & Neustadt, P.C.

(57) ABSTRACT

A composition in the form of an oil-in-water emulsion comprising, in a physiologically acceptable medium, an oily phase dispersed in an aqueous phase and comprising at least one acrylic terpolymer obtained from the polymerization of a carboxylic acid monomer having α,β-ethylenic unsaturation, a non-surface-active monomer comprising ethylenic unsaturation other than (a), and a non-ionic urethane monomer which is the reaction product of a monohydric non-ionic amphiphilic compound with an isocyanate comprising monoethylenic unsaturation, in which the terpolymer/oily phase ratio by weight ranges from 1/50 to 1/125. The composition is particularly suited for cosmetic and/or dermatological applications.

18 Claims, No Drawings

COMPOSITION IN THE FORM OF AN OIL-IN-WATER EMULSION COMPRISING AN ACRYLIC TERPOLYMER AND ITS USES, IN PARTICULAR ITS COSMETIC USES

BACKGROUND OF THE INVENTION

1. Field of the Invention

The present application relates to a composition in the form of an oil-in-water emulsion comprising at least one acrylic terpolymer and to the use of the composition, in particular for caring for and/or treating the skin of the body or of the face, the hair and/or the lips and especially for caring for dry skin and/or dry lips.

2. Discussion of the Background

For various reasons relating in particular to better comfort of use (softness, emollience and others), current cosmetic compositions are generally provided in the form of an emulsion of the oil-in-water (O/W) type composed of a continuous aqueous dispersing phase and of a non-continuous oily dispersed phase or of an emulsion of the water-in-oil (W/O) type composed of a continuous oily dispersing phase and of a non-continuous aqueous dispersed phase. O/W emulsions are the most in demand in the cosmetics field because they comprise an aqueous phase as external phase, where the aqueous phase confers, during application to the skin, a fresher, less greasy and lighter feel than W/O emulsions.

The emulsions are generally stabilized by appropriate emulsifying surfactants which, by virtue of their amphiphilic structure, become positioned at the oil/water interface and thus stabilize the dispersed droplets. These emulsifiers exhibit the disadvantage, however, of being penetrating and potentially irritating to the skin, eyes and scalp, in particular for subjects with sensitive skin.

In addition, such emulsions can have inadequate cosmetic and physicochemical properties (oily feel, instability over time). Increasing the level of surfactants does not generally solve these problems. The required stability is not always achieved and the cosmetic properties are not improved (waxy and heavy feel and lack of freshness on application). Furthermore, as indicated above, it is also inadvisable to use an excessively high level of surfactant so as to ensure harmlessness.

One solution for achieving freedom from the phenomena of instability of the O/W emulsions (creaming and phase separation) consists in adding thickening agents to the emulsion. The function of which thickening agents is to create, within the aqueous phase, a gelled matrix which serves to set the oily droplets and which provides for mechanical maintenance of the entire emulsion. However, this solution exhibits the disadvantage of not making it possible to obtain all the desired textures and in particular fluid and light textures which are readily and rapidly applied to the skin without leaving a residual film.

Furthermore, the replacement of the surfactants by polymers comprising, in their chains, a hydrophilic part and a hydrophobic part composed of a fatty chain, such as copolymers of ($C_{10}$–$C_{30}$)alkyl acrylate and of acrylic or methacrylic acid, for example the product "Pemulen TR2" sold by Goodrich, has been envisaged. However, these polymers exhibit the disadvantage of not making it possible to obtain a composition which remains stable for a long period of time when the amount of oil is too high or when the emulsion is very fluid, that is to say in the case where the aim is to minimize the level of polymer in order not to have a thick emulsion.

SUMMARY OF THE INVENTION

An object of the present invention is to provide stable oil-in-water emulsions which optionally do not comprise an emulsifying surfactant conventionally used in O/W emulsions and which exhibit good cosmetic properties without having the disadvantages of the prior art and whatever the amount of oil present in the emulsion.

The Inventors have discovered, unexpectedly, a novel family of polymers allowing the preparation of oil-in-water emulsions which are stable although optionally devoid of conventionally used surfactant.

Thus, the present invention provides a composition in the form of an oil-in-water emulsion comprising, in a physiologically acceptable medium, an oily phase dispersed in an aqueous phase, which comprises at least one acrylic terpolymer obtained from the polymerization of (a) an $\alpha,\beta$-ethylenically unsaturated carboxylic acid monomer;

(b) a non-surface-active ethylenically unsaturated monomer other than (a); and (c) a non-ionic urethane monomer, which is the reaction product of a monohydric non-ionic amphiphilic compound with an monoethylenically unsaturated isocyanate, wherein the weight ratio of the terpolymer to the oily phase is from 1150 to 1/125.

The present invention also relates to a method of treating, protecting, caring for, removing make-up from and/or cleansing the skin, lips and/or hair and/or for making-up the skin and/or lips, comprising applying the inventive composition to the skin, lips and/or hair.

The present invention also relates to a method of cosmetically treating the skin, hair and/or lips, comprising applying the inventive composition to the skin, hair and/or lips.

A more complete appreciation of the invention and many of the attendant advantages thereof will be readily obtained as the same becomes better understood by reference to the following detailed description.

BRIEF DESCRIPTION OF THE INVENTION

The composition of the present invention has a homogeneous texture which is pleasant on application. In addition, the acrylic terpolymer used in the composition according to the invention makes it possible to prepare oil-in-water emulsions which remain stable over time at room temperature or at higher temperatures and to retain these properties of the emulsion whatever the fluidity of the emulsion and its content of oily phase. It is thus possible to prepare both thick emulsions having a high content of oily phase, which are particularly effective in the treatment of dry skin, and very fluid emulsions.

The viscosity of the emulsions can therefore vary to a large extent and can range in particular from 0.05 Pa•s to 8 Pa•s, these viscosities being measured at approximately 25° C. using a "Rheomat 180" viscometer which is generally equipped with a 2 rotor for viscosity ranges from 0.02 Pa•s to 0.7 Pa•s, with a 3 rotor for viscosity ranges from 0.2 Pa•s to 4 Pa•s, and with a 4 rotor for viscosity ranges from 2 Pa•s to 23 Pa•s. These ranges for the viscosity include all specific values and subranges therebetween, such as 0.05, 0.1, 0.5, 1, 5, 10, 12, 15 and 20 Pa•s.

The emulsion of the invention is preferably devoid of surfactant conventionally used in O/W emulsions and it exhibits, for this reason, the advantage of not being irritating to particularly sensitive skin. In addition, this emulsion exhibits the advantage of making possible the incorporation of heat-sensitive active principles as it can be manufactured at room temperature, both in the stage of neutralization of the polymer and in the stage of dispersion of the oily phase.

The acrylic terpolymer used in accordance with the invention is soluble or swellable in alkaline substances. It is preferably characterized in that it comprises, with respect to the total weight of the terpolymer:

(a) Approximately 20 to 70% by weight, preferably 25 to 55% by weight, of an α,β-monoethylenically unsaturated carboxylic acid monomer. These ranges include all specific values and subranges therebetween, such as 30, 35, 40, 45, 50, 60 and 65% by weight, (b) Approximately 20 to 80% by weight, preferably 30 to 65% by weight, of a non-surface-active monoethylenically unsaturated monomer other than (a). These ranges for the viscosity include all specific values and subranges therebetween, such as 25, 35, 40, 50, 55, 60, 70 and 75% by weight, and (c) Approximately 0.5 to 60% by weight, preferably 10 to 50% by weight, of a non-ionic urethane monomer which is the reaction product of a monohydric non-ionic amphiphilic compound with a monoethylenically unsaturated isocyanate. These ranges for the viscosity include all specific values and subranges therebetween, such as 1, 2, 5, 15, 20, 25, 30, 35, 40, 45 and 55% by weight.

The carboxylic acid comprising α,β-monoethylenic unsaturation (a) can be chosen from numerous acids and in particular acrylic acid, methacrylic acid, crotonic acid, itaconic acid and maleic acid. This monomer is preferably methacrylic acid. A large proportion of acid is preferable in order to give a polymer structure which dissolves and gives a thickener by reaction with an alkaline compound, such as sodium hydroxide, alkanolamines, aminomethylpropanol or aminomethylpropanediol.

The terpolymer comprises a monomer (b) comprising monoethylenic unsaturation which does not have a surface-active property and which is also preferably present in a high proportion, as indicated above. The preferred monomers are those which give polymers which are insoluble in water when they are homopolymerized and they are illustrated by $C_1$–$C_4$ alkyl acrylates and methacrylates, such as methyl acrylate, ethyl acrylate, butyl acrylate or the corresponding methacrylates. The more preferred monomers are methyl acrylate and ethyl acrylate. Other monomers which can be used include styrene, vinyltoluene, vinyl acetate, acrylonitrile and vinylidene chloride. Unreactive monomers are preferred, these monomers being those in which the only ethylenic group is the sole reactive group under the conditions of the polymerization. However, monomers which comprise groups which are reactive under the effect of heat, such as hydroxyethyl acrylate, can optionally be used.

The monohydric non-ionic amphiphilic compounds used to obtain the non-ionic urethane monomer (c) are well known and are generally alkoxylated hydrophobic compounds comprising an alkylene oxide forming the hydrophilic part of the molecule. The hydrophobic compounds are generally composed of an aliphatic alcohol or an alkylphenol, in which compounds a carbonaceous chain comprising at least six carbon atoms constitutes the hydrophobic part of the amphiphilic compound.

The preferred monohydric non-ionic amphiphilic compounds are compounds having the following formula (I):

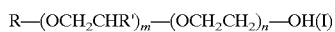

in which R is chosen from alkyl groups comprising from 6 to 30 carbon atoms and aralkyl groups where alkyl radicals comprise from 8 to 30 carbon atoms, R' is chosen from alkyl groups comprising from 1 to 4 carbon atoms, n is a mean number ranging from approximately 6 to 150 and m is a mean number ranging from approximately 0 to 50, provided that n is at least as great as m and that n+m=6 to 150.

Preferably, in the compounds of formula (I), the R group is chosen from alkyl groups comprising from 18 to 26 carbon atoms and alkylphenyl groups in which the alkyl part comprises 8 to 13 carbon atoms; the R' group is the methyl group; m=0 and n=6 to 150. The compound of formula (I) can be in particular an oxyalkylenated derivative, in particular an oxyethylenated derivative, of an aliphatic alcohol of vegetable origin and in particular of behenyl alcohol, the R radical in the formula (I) then being the behenyl radical.

The monoethylenically unsaturated isocyanate used to form the non-ionic urethane monomer (c) can be chosen from highly varied compounds. Use may be made of any compound comprising a copolymerizable unsaturation, such as an acrylic, methacrylic or allylic unsaturation. The preferred isocyanate having monoethylenic unsaturation is α,β-dimethyl-m-isopropenylbenzyl isocyanate.

The acrylic terpolymer defined above is obtained by copolymerization in aqueous dispersion of the components (a), (b) and (c), which copolymerization is conventional and is disclosed, for example, in EP-A-0,173,109, incorporated herein by reference.

Examples of terpolymers which can be used in the present invention, include the reaction product of methacrylic acid, as component (a), of ethyl acrylate, as component (b), and of a non-ionic urethane macromonomer having the following structure (II):

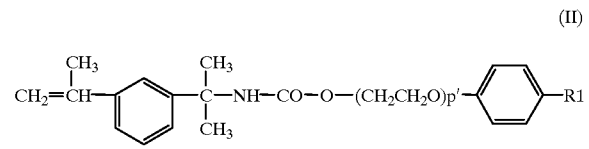

in which p' ranges from 6 to 150 and is preferably equal to 30 and R1 is chosen from alkyl radicals comprising from 8 to 13 carbon atoms, as described in Example 3 of EP-A-0, 173,109, as component (c).

The preferred acrylic terpolymer used in the invention is obtained from methacrylic acid, as component (a), from methyl acrylate, as component (b), and from a non-ionic urethane macromonomer having the following structure (III):

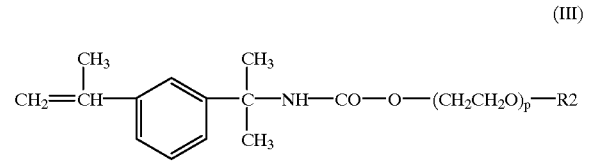

in which p ranges from 6 to 150 and R2 is chosen from linear alkyl radicals comprising from 18 to 26 and preferably from 20 to 24 carbon atoms, as component (c). Preferably, the R2 radical in the compound of formula (III) is a radical of vegetable origin, such as the behenyl radical.

The terpolymers used according to the invention are generally in aqueous dispersion.

Use may in particular be made, as terpolymer, of the terpolymer obtained from acrylic acid, from methyl acrylate and from the compound of formula (III) where p is 40 and R2 is the behenyl radical. This is the methacrylic acid/ methyl acrylate/dimethyl-m-isopropenylbenzyl isocyanate of behenyl alcohol ethoxylated with 40 EO terpolymer, i.e., comprises 40 oxyethylene groups.

The acrylic terpolymer is present in the composition of the invention in concentrations as active material which can vary according to the concentration of oil and according to the desired viscosity. The concentration as active material of terpolymer preferably ranges from 0.01 to 3% by weight, better still from 0.05 to 1% by weight and preferably from 0.2 to 0.5% by weight with respect to the total weight of the composition. These ranges include all specific values and subranges therebetween, such as 0.02, 0.1, 0.8, 1.0, 1.5, 2.0 and 2.5% by weight.

For the preparation of very fluid emulsions, the amount of terpolymer as active material preferably ranges from 0.05 to 1% and better still from 0.15 to 0.5% by weight with respect to the total weight of the composition and, for the preparation of oil-rich compositions, that is to say comprising at least 40% of oils, the amount of terpolymer as active material preferably ranges from 0.4 to 1% and better still from 0.5 to 0.7% by weight with respect to the total weight of the composition.

In the composition according to the invention, the terpolymer/oily phase ratio ranges from 1/50 to 1/125. For the preparation of very fluid emulsions, this ratio preferably ranges from 1/50 to 1/100 and better still from 1/60 to 1/100. When the amount of oily phase is high (at least 40% by weight), this ratio preferably ranges from 1175 to 1/125. These ranges include all specific values and subranges therebetween, such as 1/55, 1/65, 1/85, 1/95, 1/105, 1/110, 1/115 and 1/120.

According to a specific embodiment of the invention, the composition of the invention does not comprise polymers other than the terpolymer.

The oily phase of the composition according to the invention generally represents from 1 to 80% and preferably from 10 to 60% by weight with respect to the total weight of the composition. These ranges include all specific values and subranges therebetween, such as 2, 5, 15, 25, 30, 40 and 50% by weight.

For the preparation of very fluid emulsions, the amount of oily phase preferably ranges from 1 to 30% and better still from 10 to 25% by weight with respect to the total weight of the composition and, for the preparation of oil-rich compositions, the amount of oily phase is preferably greater than 40% and generally ranges from 40 to 80% and better still from 50 to 60% by weight with respect to the total weight of the composition.

The nature of the oily phase of the emulsion according to the invention is not critical, and may vary widely. The oily phase can thus be composed of any fatty substance and in particular oils conventionally used in the cosmetics or dermatological fields.

Mention may be made, among oils which can be used in the emulsion of the invention of, for example, vegetable oils, such as jojoba oil, avocado oil, sweet almond oil, apricot oil, maize oil and the liquid fraction of karite butter; mineral oils, such as liquid petrolatum; synthetic oils, such as 2-ethylhexyl palmitate, isopropyl myristate, hydrogenated isoparaffin, isononyl isononanoate or cetearyl octanoate; volatile or non-volatile silicone oils; and fluorinated oils. The other fatty substances which can be present in the oily phase can be, for example, fatty acids, fatty alcohols and waxes.

According to a specific embodiment of the invention, the composition of the invention comprises at least one silicone oil, preferably a volatile silicone oil, which can be chosen, for example, from cyclic or linear polydimethylsiloxanes and their mixtures. The cyclic polydimethylsiloxanes or cyclomethicones comprise from approximately 3 to 9 silicon atoms and preferably from 4 to 6 silicon atoms and can be, for example, cyclohexadimethylsiloxane and cyclopentadimethylsiloxane. The volatile linear polydimethylsiloxanes preferably comprise from approximately 3 to 9 silicon atoms. The volatile linear polydimethylsiloxanes generally have a viscosity at 25° C. of less than or equal to 5 cSt, whereas the cyclomethicones generally have a viscosity at 25° C. of less than or equal to 10 cSt.

The composition according to the invention comprises a physiologically acceptable medium, i.e., a medium compatible with the skin, lips, scalp, eyes and/or hair.

In a known way, the compositions of the invention can comprise adjuvants usual in the fields under consideration, such as hydrophilic or lipophilic active principles, preservatives, antioxidants, fragrances, solvents, fillers (kaolin), screening agents, colouring materials, basic agents (triethanolamine, sodium hydroxide), acidic agents and lipid vesicles. These adjuvants are used in the proportions usual in the cosmetics field, for example from 0.01 to 30% of the total weight of the emulsion, and they are, depending on their nature, introduced into the aqueous phase or into the oily phase of the emulsion or into vesicles. These adjuvants and their concentrations must be such that they do not modify the property desired for the emulsion of the invention.

Examples of solvents include linear or branched monoalcohols having from 1 to 8 carbon atoms, such as ethanol, propanol, butanol, isopropanol or isobutanol; polyethylene glycols having from 6 to 80 ethylene oxides; or polyols, such as propylene glycol, isoprene glycol and butylene glycol.

Examples of active principles include moisturizers, such as polyols, for example glycerol and sorbitol; keratolytic agents; depigmenting agents; slimming agents; and any active principle appropriate for the final aim of the composition.

According to a specific form of the invention, the composition of the invention may be devoid of metal oxide nanopigments.

The composition preferably exhibits a pH which has respect for the skin and which is compatible with the terpolymers used. The pH of the composition generally ranges from 6.5 to 8 and preferably from 7 to 7.5. These ranges for the pH include all specific values and subranges therebetween, such as 6.6, 6.75, 6.9, 7.1, 7.25 and 7.4.

As indicated above, the compositions according to the invention can be more or less fluid and they can therefore be provided in the form of a serum, milk, cream or paste. These compositions are prepared according to the usual methods.

The compositions of the invention may be used in a large number of cosmetic treatments of the skin, lips and hair, including the scalp, in particular for treating, protecting, caring for, removing make-up from and/or cleansing the skin, lips and/or hair and/or for making-up the skin and/or lips. They can also be intended for treating dry skin and/or dry lips.

The compositions of the invention can be used, for example as care, make-up removing and/or cleansing products for the face in the form of creams or milks or as make-up products (skin and lips) by incorporation of fillers or colorants.

An aspect of the invention is consequently the cosmetic use of the composition as defined above for treating, protecting, caring for, removing make-up from and/or cleansing the skin, lips and/or hair and/or for making-up the skin and/or lips.

Another aspect of the invention is the use of the composition as defined above in the manufacture of a composition intended for caring for dry skin and/or dry lips.

Another aspect of the invention is a process for the cosmetic treatment of the skin, including the scalp, hair and/or lips, characterized in that a composition as defined above is applied to the skin, hair and/or lips.

EXAMPLES

The examples which follow will make possible a better understanding of the invention without, however, limiting the scope thereof. The amounts shown are as % by weight, except when noted otherwise.

Example 1

| Care Milk for the Body and Face | |
|---|---|
| Phase A | |
| Methacrylic acid/methyl acrylate/dimethyl-m-isopropenylbenzyl isocyanate of behenyl alcohol ethoxylated with 40 EO terpolymer, as 24% aqueous dispersion | 2.1% (i.e. 0.5% of active material) |
| Sodium hydroxide | 0.09% |
| Preservatives | 0.15% |
| Demineralized water | q.s. for 100% |
| Phase B | |
| Cyclomethicone (cyclopentasiloxane) | 15% |
| Sweet almond oil | 15% |

Procedure: The sodium hydroxide is added to the polymer with stirring and the emulsion is prepared by pouring the phase B into the phase A with stirring. Homogenization is subsequently carried out under pressure (500 bar).

A fluid emulsion is obtained which is particularly suitable as moisturizing product. The feel is very fresh and non-greasy.

Example 2

| Make-up Removing Emulsion | |
|---|---|
| Phase A | |
| Methacrylic acid/methyl acrylate/dimethyl-m-isopropenylbenzyl isocyanate of behenyl alcohol ethoxylated with 40 EO terpolymer, as 24% aqueous dispersion | 1.25% (i.e. 0.3% of active material) |
| Sodium hydroxide | 0.06% |
| Preservatives | 0.2% |
| Isoprene glycol | 5% |
| Demineralized water | q.s. for 100% |
| Phase B | |
| 2-Ethylhexyl palmitate | 20% |
| Liquid petrolatum | 7% |

The procedure is identical to that of Example 1.

An emulsion is obtained which is suitable for removing make-up from the face and from the eyes. Its viscosity is suitable for packaging of bottle type because it has a gelled appearance at rest but flows very easily as soon as the bottle is shaken. Its viscosity is 0.25 Pa·s (2.5 poises) on a Rheomat 180, 2 rotor.

Example 3

| Night Moisturizing Cream for the Face | |
|---|---|
| Phase A | |
| Methacrylic acid/methyl acrylate/dimethyl-m-isopropenylbenzyl isocyanate of behenyl alcohol ethoxylated with 40 EO terpolymer, as 24% aqueous dispersion | 1.68% (i.e. 0.4% of active material) |
| Sodium hydroxide | 0.07% |
| Preservatives | 0.1% |
| Glycerol | 7% |
| Demineralized water | q.s. for 100% |
| Phase B | |
| Liquid fraction of karite butter | 15% |
| Cyclomethicone (cyclopentasiloxane) | 10% |
| Hydrogenated isoparaffin | 15% |

The procedure is identical to that of Example 1.

A moisturizing cream is obtained which is very comfortable, even on normal skin with a tendency towards greasiness, despite the high percentage of oils.

Example 4

| Nourishing and Moisturizing Cream for Dry Skin | |
|---|---|
| Phase A | |
| Methacrylic acid/methyl acrylate/dimethyl-m-isopropenylbenzyl isocyanate of behenyl alcohol ethoxylated with 40 EO terpolymer, as 24% aqueous dispersion | 2.1% (i.e. 0.5% of active material) |
| Sodium hydroxide | 0.09% |
| Preservatives | 0.2% |
| Glycerol | 2% |
| Demineralized water | q.s. for 100% |
| Phase B | |
| Liquid petrolatum | 15% |
| Liquid fraction of karite butter | 20% |
| Cyclomethicone (cyclopentasiloxane) | 15% |
| Fragrance | 0.4% |

The procedure is identical to that of Example 1.

An emulsion is obtained which is particularly suitable for the preparation of night creams. The feel is not greasy despite the high percentage of oil.

Example 5

| Make-up Removing Cream | |
|---|---|
| Phase A | |
| Methacrylic acid/methyl acrylate/dimethyl-m-isopropenylbenzyl isocyanate of behenyl alcohol ethoxylated with 40 EO terpolymer, as 24% aqueous dispersion | 2.1% (i.e. 0.5% of active material) |
| Sodium hydroxide | 0.09% |
| Preservatives | 0.2% |
| Glycerol | 2% |
| Demineralized water | q.s. for 100% |
| Phase B | |
| Liquid petrolatum | 25% |
| Silicone oil (Dimethicone 10 cSt) | 15% |
| Isononyl isononanoate | 20% |

The procedure is identical to that of Example 1.

A cream is obtained which is particularly effective in removing waterproof mascaras and transfer-free make-up products. It is removed either by rinsing or simply by wiping.

Comparative Examples 1 and 2

The terpolymer used according to the invention was replaced, in the composition of Example 5, by a polyacrylamide (Hostacerin AMPS; CTFA name: Ammonium polyacryldimethyltauramide) (Comparative Example 1) or Pemulen TR2 (Comparative Example 2). The following results were obtained:

| Composition | Example 5 | Comparative Example 1 | Comparative Example 2 |
|---|---|---|---|
| pH at room temperature (20–25° C.) | 7.05 | 7.25 | 6.7 |
| Stability | Very fine emulsion Thick texture Stable at all temperatures | Coarse emulsion* Very fluid texture Destabilized after 4 weeks at 45° C. | Coarse emulsion* Fairly fluid texture Release of water at the surface after 2 months at 20–25° C. |
| Viscosity at T0 at approximately 25° C. on a Rheomat 180 | 4.7 Pa·s (4 rotor) | 0.131 Pa·s (2 rotor) | 0.9 Pa·s (3 rotor) |

*a coarse emulsion is an emulsion comprising large oily globules, that is to say globules having a mean size of greater than 20 microns.

It emerges from the above table that the polyacrylamide and the Pemulen TR2 do not make it possible to obtain these thick cream textures comprising a high level of oil which are stable at a pH in the vicinity of neutrality.

Example 6

| Mask | |
|---|---|
| Phase A | |
| Methacrylic acid/methyl acrylate/dimethyl-m-isopropenylbenzyl isocyanate of behenyl alcohol ethoxylated with 40 EO terpolymer, as 24% aqueous dispersion | 1.67% (i.e. 0.4% of active material) |
| Sodium hydroxide | 0.07% |
| Kaolin | 15% |
| Preservatives | 0.3% |
| Glycerol | 10% |
| Demineralized water | q.s. for 100% |
| Phase B | |
| Maize oil | 15% |
| Cyclomethicone (cyclopentasiloxane) | 10% |
| Cetearyl octanoate | 10% |

The procedure is identical to that of Example 1.

A mask is obtained which is particularly well tolerated by sensitive skin. It is rinsed off or is wiped off after leaving on the skin for a few minutes.

Obviously, numerous modifications and variations of the present invention are possible in light of the above teachings. It is therefore to be understood that within the scope of the appended claims, the invention may be practiced otherwise than as specifically described herein.

This application is based on French Patent Application Serial No. 99-03320, filed on Mar. 17, 1999, and incorporated herein by reference in its entirety.

What is claimed is:

1. A composition in the form of an oil-in-water emulsion comprising, in a physiologically acceptable medium, an oily phase dispersed in an aqueous phase, which comprises at least one acrylic terpolymer obtained from the polymerization of
    (a) an α,β-ethylenically unsaturated carboxylic acid monomer;
    (b) a non-surface-active ethylenically unsaturated monomer other than (a); and
    (c) a non-ionic urethane monomer, which is the reaction product of a monohydric non-ionic amphiphilic compound with an monoethylenically unsaturated isocyanate,
wherein the weight ratio of the terpolymer to the oily phase is from 1/50 to 1/125.

2. The composition of claim 1, which is devoid of surfactant.

3. The composition of claim 1, wherein the acrylic terpolymer comprises, with respect to the total weight of the terpolymer:
    approximately from 20 to 70% by weight of (a);
    approximately from 20 to 80% by weight of (b); and
    approximately from 0.5 to 60% by weight of (c).

4. The composition of claim 1, wherein (a) is selected from the group consisting of acrylic acid, methacrylic acid, crotonic acid, itaconic acid and maleic acid.

5. The composition of claim 1, wherein (a) is methacrylic acid.

6. The composition of claim 1, wherein (b) is selected from the group consisting of $C_1$–$C_4$ alkyl acrylates and methacrylates, styrene, vinyltoluene, vinyl acetate, acrylonitrile and vinylidene chloride.

7. The composition of claim 1, wherein (b) is methyl acrylate or ethyl acrylate.

8. The composition of claim 1, wherein the monohydric non-ionic amphiphilic compound used to produce the non-ionic urethane monomer is a compound represented by formula (I):

$$R\text{—}(OCH_2CHR')_m\text{—}(OCH_2CH_2)_n\text{—}OH \qquad (I)$$

wherein
    R is selected from the group consisting of alkyl groups comprising from 6 to 30 carbon atoms and aralkyl groups comprising from 8 to 30 carbon atoms;
    R' is selected from the group consisting of alkyl groups comprising from 1 to 4 carbon atoms;
    n is a mean number ranging from approximately 6 to 150; and
    m is a mean number ranging from approximately 0 to 50, provided that n is at least as great as m and that n+m=6 to 150.

9. The composition of claim 8, wherein
    R is selected from the group consisting of alkyl groups comprising from 18 to 26 carbon atoms and alkylphenyl groups in which the alkyl part comprises 8 to 13 carbon atoms;
    R' is methyl;
    m=0; and
    n=6 to 150.

10. The composition of claim 1, wherein isocyanate is α,α-dimethyl-m-isopropenylbenzyl isocyanate.

11. The composition of claim 1, wherein
(a) is methacrylic acid;
(b) is methyl acrylate; and
(c) is represented by formula (III):

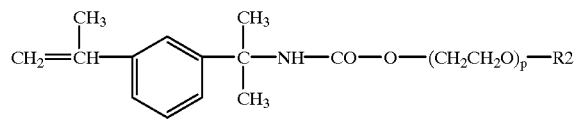

wherein
p is 6 to 150; and
R2 is selected from the group consisting of linear alkyl radicals comprising from 18 to 26 carbon atoms.

12. The composition of claim 1, comprising 0.01 to 3% by weight of the terpolymer.

13. The composition of claim 1, comprising 1 to 80% by weight of the oily phase.

14. The composition of claim 1, which comprises at least one volatile silicone oil.

15. The composition of claim 1, which has a pH ranging from 6.5 to 8.

16. A method of treating, protecting, caring for, removing make-up from and/or cleansing the skin, lips and/or hair and/or for making-up the skin and/or lips, comprising applying the composition of claim 1 to the skin, lips and/or hair.

17. The method of claim 16, comprising applying the composition to dry skin and/or dry lips.

18. A method of cosmetically treating the skin, hair and/or lips, comprising applying the composition of claim 1 to the skin, hair and/or lips.

* * * * *

UNITED STATES PATENT AND TRADEMARK OFFICE
CERTIFICATE OF CORRECTION

PATENT NO. : 6,228,348 B1
DATED : May 8, 2001
INVENTOR(S) : Pascal Simon et al.

It is certified that error appears in the above-identified patent and that said Letters Patent is hereby corrected as shown below:

Title page,
-- [30] Foreign Application Priority Data
March 17, 1999    (FR)........................ 99 03320 --;

Column 10,
Line 65, "6to" should read -- 6 to --.

Signed and Sealed this

Twenty-sixth Day of March, 2002

Attest:

JAMES E. ROGAN
*Attesting Officer*    *Director of the United States Patent and Trademark Office*